Aug. 29, 1961 H. M. TIRET Plant Pat. 2,083
FUCHSIA PLANT
Filed Nov. 8, 1960
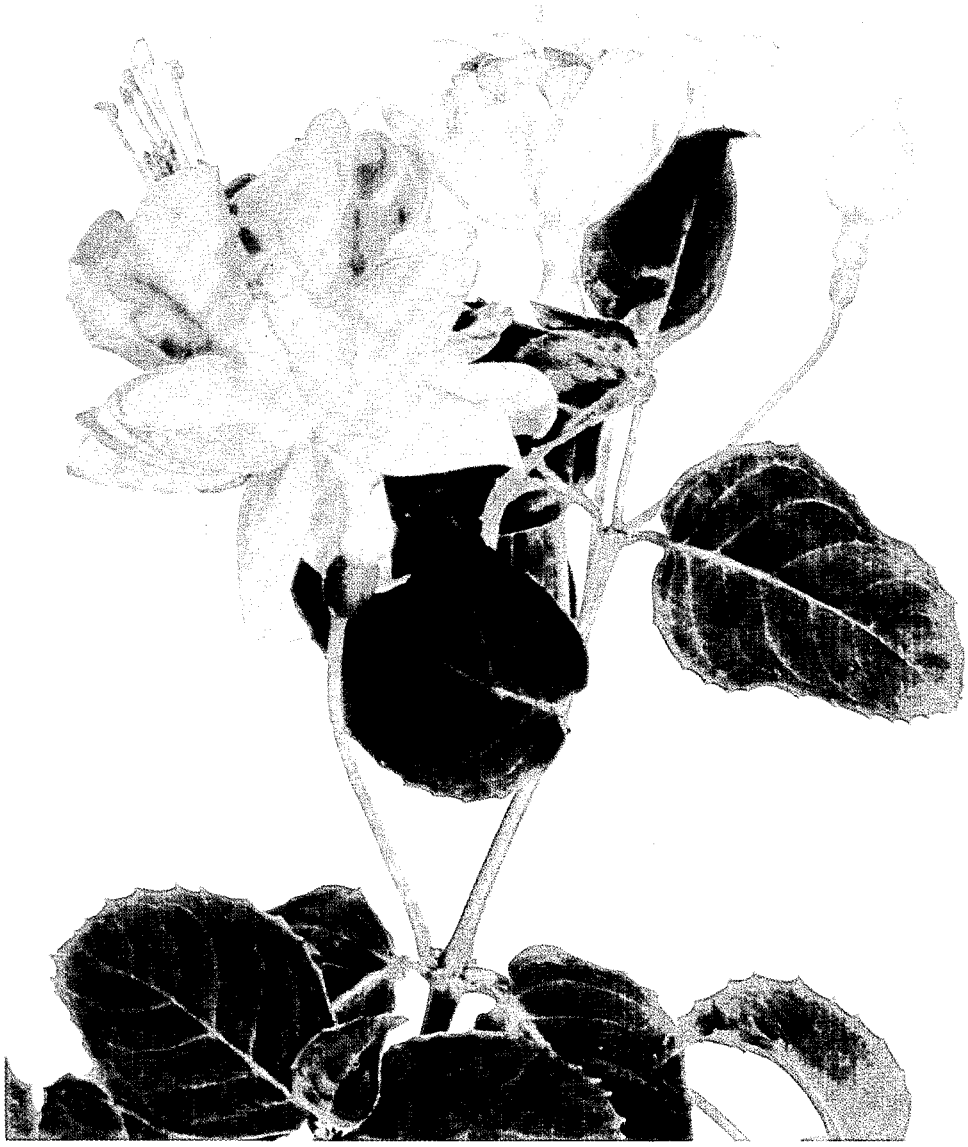

United States Patent Office

Plant Pat. 2,083
Patented Aug. 29, 1961

2,083
FUCHSIA PLANT

Horace M. Tiret, San Francisco, Calif.

Filed Nov. 8, 1960, Ser. No. 68,141
1 Claim. (Cl. 47—60)

This invention relates to a new and improved fuchsia plant, the principal new and different characteristics of which are the contrast of the Carmine Rose outer petals with the Tyrian Rose main petals in the mature flower, combined in a classical form.

The accompanying drawing illustrates the plant in bloom and the aforementioned new and different characteristics.

The plant was derived as a hybrid from a seedling (unpatented) not introduced to the trade, namely 11–67–3 (figures representing applicant's own breeding symbols) and a seedling (unpatented) 11–42–12. The plant has been asexually reproduced at Colma, California, by cuttings which retained the characteristics of the parent fuchsia plant.

The plant is a vigorous, upright grower. It is a heavy, early bloomer.

In the accompanying drawing, the figure shows a typical branch tip represented in approximate actual size.

A detailed description of the new variety of fuchsia plant follows (all measurements approximate):

*Habit of growth.*—Vigorous, upright variety. Early bloomer and profuse self-brancher.

*Foliage.*—The leaves are dark green, medium small in size, medium veined surface. The mature leaf is approximately 2 5/16″ in length and 1½″ in width at the broadest point. Texture of the leaf is crinkly (medium). Branches are dark reddish-brown.

*Buds.*—Color of buds is Venetian Pink (British Horticultural Color Chart #420/3), with green tips. Length from the ovary is approximately 1½″. Width at the broadest point is ¾″.

*Ovary.*—Color of the ovary is green (solid). Length is ⅜″. Width at the broadest point, at maturity, is ¼″.

*Sepals.*—There are 4 sepals, each 1½″ in length and ⅝″ in width at the broadest point. Form is medium broad and recurved. The texture of the underside cupe (slight) and the outer surface is smooth and satiny. Color of the underside is Carmine Rose (British Horticultural Chart #621/1), with green tips.

*Tube.*—Medium long and slender. Length is 1″, width 3/16″ at the broadest point. Color is white with greenish cast.

*Stamens.*—There are 8 stamens, colored rose, with deeper rose on the anthers. Form is medium slender, length is 1¾″.

*Pistil.*—The style is 2¾″ in length, 1/32″ in width. The color is rosy pink, the stigma creamy white.

*Petals.*—Color of the outer petals is Carmine Rose (British Horticultural Color Chart #621/1), flushed at the tips with a darker Tyrian Rose (British Horticultural Color Chart #24/1). As the flower matures the main petals develop the same color characteristics as the outer petals. When the flower opens the main petals are Mauve (British Horticultural Color Chart #633).

The petals are 23 in number. They are medium large, with fully open corolla. Position of the petals is vertical for the center and horizontal for the outer, which results in a flaring form. The diameter of the fully open mature flower is 2½″. The large petals are 1½″ in length and width. The texture is smooth.

*Parentage.*—Applicant's own seedlings (unpatented) not introduced to the trade, 11–67–3, and 11–42–12 (applicant's own breeding symbols).

Having thus disclosed my discovery, I claim:

A new and distinct variety of fuchsia plant, substantially as herein shown and described, characterized by the Carmine Rose coloring of the outer petals and the Tyrian Rose center petals, combined in a classic, symmetrical form in a plant which has vigorous, upright growth characteristics.

No references cited.